(12) United States Patent
Matsumura (10) Patent No.: US 8,974,746 B2
(45) Date of Patent: Mar. 10, 2015

(54) BIOLOGICAL SAMPLE MEASURING DEVICE FOR MEDICAL INSTITUTIONS

(75) Inventor: Keisuke Matsumura, Ehime (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 0 days.

(21) Appl. No.: 13/822,576

(22) PCT Filed: Sep. 8, 2011

(86) PCT No.: PCT/JP2011/005046
§ 371 (c)(1),
(2), (4) Date: Mar. 12, 2013

(87) PCT Pub. No.: WO2012/035725
PCT Pub. Date: Mar. 22, 2012

(65) Prior Publication Data
US 2013/0184548 A1 Jul. 18, 2013

(30) Foreign Application Priority Data

Sep. 16, 2010 (JP) ................. 2010-207496

(51) Int. Cl.
| G01N 33/00 | (2006.01) |
| A61B 5/00 | (2006.01) |
| G01N 35/00 | (2006.01) |
| A61B 5/145 | (2006.01) |

(52) U.S. Cl.
CPC ........ *A61B 5/7445* (2013.01); *G01N 35/00663* (2013.01); *G01N 2035/009* (2013.01); *G01N 2035/0091* (2013.01); *A61B 5/14532* (2013.01); *A61B 5/743* (2013.01)
USPC ......................................... 422/404; 422/400

(58) Field of Classification Search
USPC .................................................. 422/400, 404
See application file for complete search history.

(56) References Cited

U.S. PATENT DOCUMENTS

| 6,635,167 B1 | 10/2003 | Batman et al. |
| 7,912,655 B2 | 3/2011 | Power et al. |
| 7,942,844 B2 | 5/2011 | Moberg et al. |
| 2007/0255125 A1 | 11/2007 | Moberg et al. |
| 2007/0255250 A1 | 11/2007 | Moberg et al. |
| 2009/0093972 A1 | 4/2009 | Power et al. |

(Continued)

FOREIGN PATENT DOCUMENTS

| JP | 8-153290 | 6/1996 |
| JP | 2001-525588 | 12/2001 |

(Continued)

OTHER PUBLICATIONS

International Search Report issued Nov. 29, 2011 in International (PCT) Application No. PCT/JP2011/005046.

*Primary Examiner* — Sam P Siefke
(74) *Attorney, Agent, or Firm* — Wenderoth, Lind & Ponack, L.L.P.

(57) ABSTRACT

A biological sample measuring device has the display screen of a display section divided into a first display area that displays measurement values, and a second displays area that displays the operating status. When the scheduled maintenance is needed for the biological sample measuring device, a controller displays an scheduled maintenance warning in the first and second display areas upon the first start-up that day, and displays an scheduled maintenance warning only in the second display area upon the second and subsequent start-ups that day.

10 Claims, 7 Drawing Sheets

(56) References Cited

U.S. PATENT DOCUMENTS

2009/0177769 A1* 7/2009 Roberts .................. 709/224
2010/0331650 A1* 12/2010 Batman et al. ........... 600/365
2011/0137571 A1 6/2011 Power et al.

FOREIGN PATENT DOCUMENTS

| JP | 2003-215122 | 7/2003 |
| JP | 2009-502438 | 1/2009 |
| JP | 2009-535715 | 10/2009 |

* cited by examiner

BIOLOGICAL SAMPLE MEASURING DEVICE FOR MEDICAL INSTITUTIONS

BACKGROUND

1 Technical Field

The present invention relates to a biological sample measuring device for medical institutions, which measures blood glucose levels, lactic acid levels, and so forth in biological samples, for example.

2 Background Art

In recent years, biological sample measuring devices used by nurses and so forth to measure glucose levels, lactic acid levels, and the like in biological samples at hospitals and other such medical institutions have had the following configuration.

Specifically, a conventional biological sample measuring device comprises a main body case, a display section provided to the main body case, a controller connected to the display section, a measurement section connected to the controller, and a sensor mounting portion connected to this measurement section. Measurement values for blood glucose levels and so forth measured by the measurement section are displayed on the display section.

With a biological sample measuring device such as this, a quality control scheduled maintenance is provided and measurements to check the operation are carried out periodically in order to improve the measurement reliability.

More specifically, measurements to check the operation are carried out periodically by mounting an accuracy management chip to the sensor mounting portion (see Patent Literature 1, for example), or depositing a control solution onto a sensor mounted to the sensor mounting portion.

CITATION LIST

Patent Literature

Japanese Laid-Open Patent Application 2003-215122

SUMMARY

However, the following problems were encountered with the conventional biological sample measuring device discussed above.

Specifically, with the above-mentioned conventional configuration, whenever the quality control scheduled maintenance draws near, a warning display that warns the user that the scheduled maintenance is approaching is displayed on the display section. This prompts the user to carry out measurements to check the operation of the device, allowing periodic operation checks to be performed and the scheduled maintenance to be updated. As a result, the scheduled maintenance of the biological sample measuring device will not be exceeded.

However, with a conventional biological sample measuring device such as this, since a warning is displayed every time the device is used, this is inconvenient when measurements are repeatedly taken for a plurality of patients at a hospital or other such medical institution.

More specifically, blood glucose must be measured two hours after eating, but since meals are usually all served at the same time in a hospital or other such medical institution, the measurements of blood glucose levels all have to be carried out within the same specific time frame, which can result in the people who measure blood glucose levels being extremely busy during these time periods.

With a conventional biological sample measuring device, even though the user may be very busy, the warning display still ends up appearing every time the device is used when the scheduled maintenance is near. Accordingly, the user has to measure the blood glucose level after first canceling this warning display, which makes the device very inconvenient to use.

In view of this, it is an object of the present invention to provide a biological sample measuring device that is convenient to use even when used repeatedly in a specific time slot at a hospital or other such medical institution, for example.

To achieve the stated object, the biological sample measuring device for medical institutions of the present invention comprises a main body case, a sensor mounting portion, a measurement section, a display section, and a controller. The sensor mounting portion is provided to a first end of the main body case, and to it is mounted a sensor for measuring biological samples. The measurement section is connected to the sensor mounting portion and is used to measure biological samples. The display section has a display screen provided to the outer surface of the main body case, with this display screen being divided into a first display area for displaying the biological sample measurement values, and a second display area for displaying an operating status. The controller displays scheduled maintenance warnings in the first display area and second display area at the initial start-up that satisfies a specific condition on the scheduled maintenance or shortly before, and displays the scheduled maintenance warning only in the second display area at the second and subsequent start-ups.

Because the biological sample measuring device of the present invention is configured as above, when the device is used in a hospital or other such medical institution, even on or near the scheduled maintenance, unless a specific condition is met, a warning is displayed in the first display area, in which measurement values are displayed, only the first time the device is turned on, after which an scheduled maintenance warning is displayed only in the second display area. Therefore, the user does not have to waste time canceling the warning display every time, which makes the device more convenient to use than in the past.

Also, when the biological sample measuring device being used is at or near the scheduled maintenance, a warning is always displayed in the second display area unless measurement is performed to check the operating status. Consequently, the warning is displayed as little as possible in the first display area, while the warning is always displayed in the second display area, which prevents the biological sample measuring device from becoming unusable when the scheduled maintenance is reached.

DETAIL DESCRIPTION

The biological sample measuring device pertaining to an embodiment of the present invention will now be described through reference to the drawings.

Figure 1:
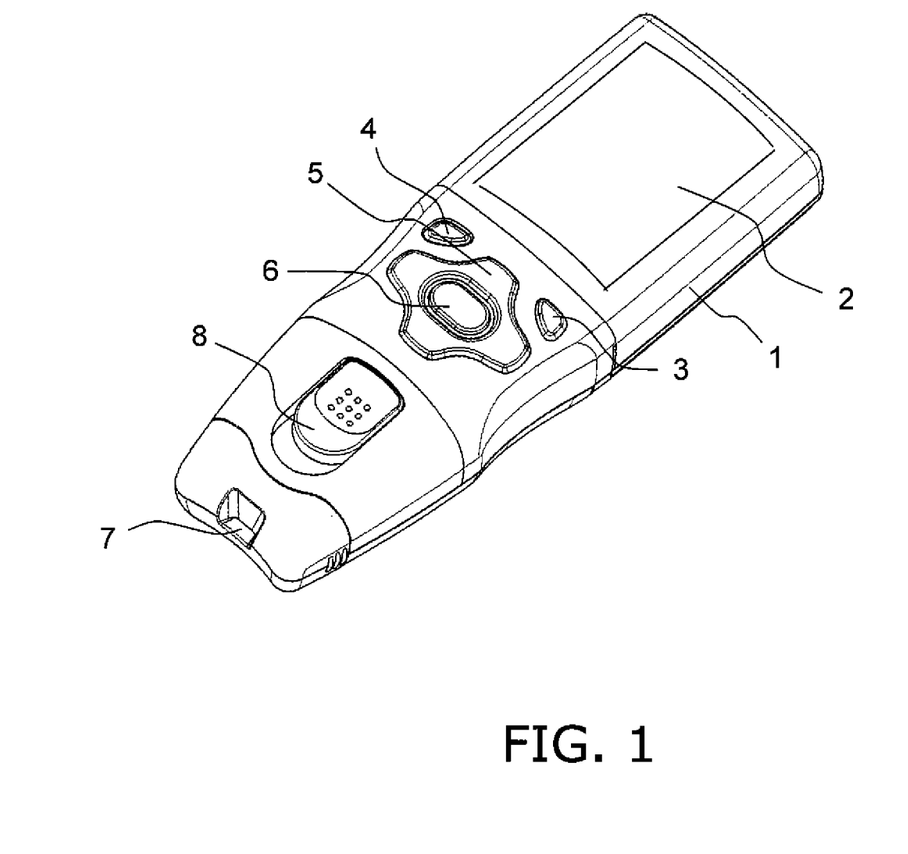
FIG. 1 is an oblique view of the biological sample measuring device for medical institutions pertaining to an embodiment of the present invention.

As shown in FIG. 1, the biological sample measuring device in this embodiment comprises a main body case 1, a display section 2, a power button 3, a menu button 4, cross key 5, an enter button 6, a sensor insertion opening 7, and a sensor eject lever 8.

The display section 2, the power button 3, the menu button 4, the cross key 5, and the enter button 6 are provided on the front of the main body case 1.

The sensor insertion opening 7 is provided at the end of the main body case 1 on the opposite side from the display section 2.

A sensor (not shown) for measuring blood glucose, for example, is inserted into the sensor insertion opening 7.

The sensor eject lever 8 is operated toward the sensor insertion opening 7 to eject the used sensor (after measurement) from the sensor insertion opening 7. Providing the sensor eject lever 8 improves safety because a used sensor can be discarded without touching it directly with the fingers.

Figure 3:
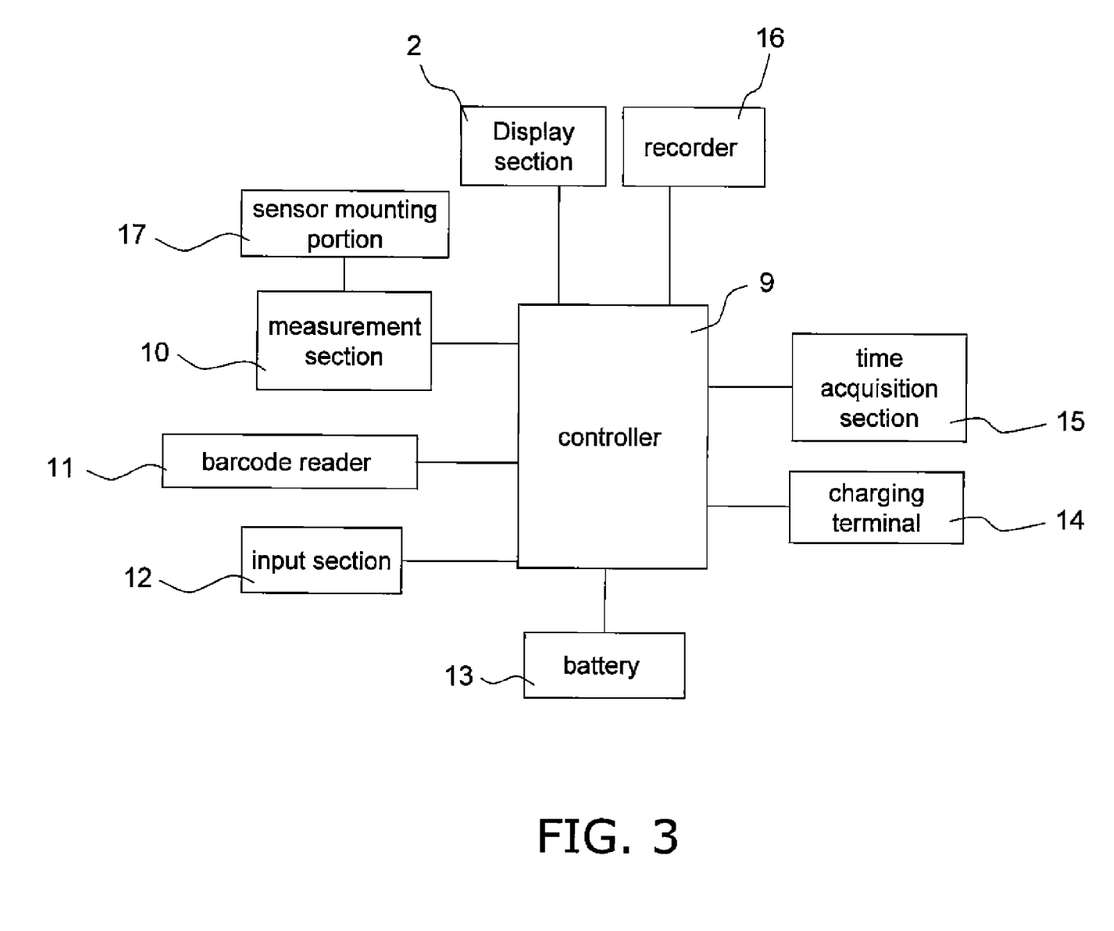
FIG. 3 is an electrical block diagram of the biological sample measuring device in FIG. 1.

The biological sample measuring device in this embodiment comprises an internal controller 9 (shown in FIG. 3).

The controller 9 connects the display section 2, a measurement section 10, a barcode reader (ID acquisition section) 11, an input section 12 (menu button 4, cross key 5, enter button 6, etc.), a battery 13, a charging terminal 14, a time acquisition section 15, and a recorder 16.

As shown in FIG. 3, the measurement section 10 is connected to a sensor mounting portion 17.

The sensor mounting portion 17 is disposed on the inside of the sensor insertion opening 7.

Specifically, when the sensor is inserted into the sensor insertion opening 7, this results in a state in which the sensor is mounted to the sensor mounting portion 17.

If it is detected that a sensor has been mounted to the sensor mounting portion 17, the main power supply of the biological sample measuring device is turned on, the sensor and the measurement section 10 are electrically connected via a connector (not shown) inside the sensor mounting portion 17, and the device is ready for the measurement of blood glucose or the like.

After this, a biological sample that has been deposited on the sensor is measured by the measurement section 10 via the sensor mounting portion 17.

As will be discussed below, the measured blood glucose level, for example, is recorded along with time information obtained from the time acquisition section 15 to the recorder 16.

Quality control information, such as the scheduled maintenance of the biological sample measuring device, is also recorded to the recorder 16.

The biological sample measuring device in this embodiment is used in a hospital or other such medical institution, and measurements for quality control are taken at a frequency of once a month, for example.

More specifically, after a sensor has been inserted into the sensor insertion opening 7, control solutions (reference samples exhibiting blood glucose levels of 70 mg/dL, 120 mg/dL, and 350 mg/dL) are deposited on the blood deposition portion of the sensor. The control solutions are then measured by the measurement section 10, and whether quality control is passed is determined by whether or not the proper measurement values are obtained.

If it is determined here that the biological sample measuring device is appropriate for use in a medical institution on the basis of this quality control measurement result, then the time (date and time) when the measurement was made is recorded to the recorder 16. For instance, one month from this recording date is set to be the next scheduled maintenance.

The above-mentioned sensor that uses a control solution to measure for quality control (also called QC measurement) can be the same as an ordinary sensor that measures blood glucose levels. With the biological sample measuring device in this embodiment, whether what is deposited on the sensor is blood or a control solution can be determined automatically.

Figure 2:
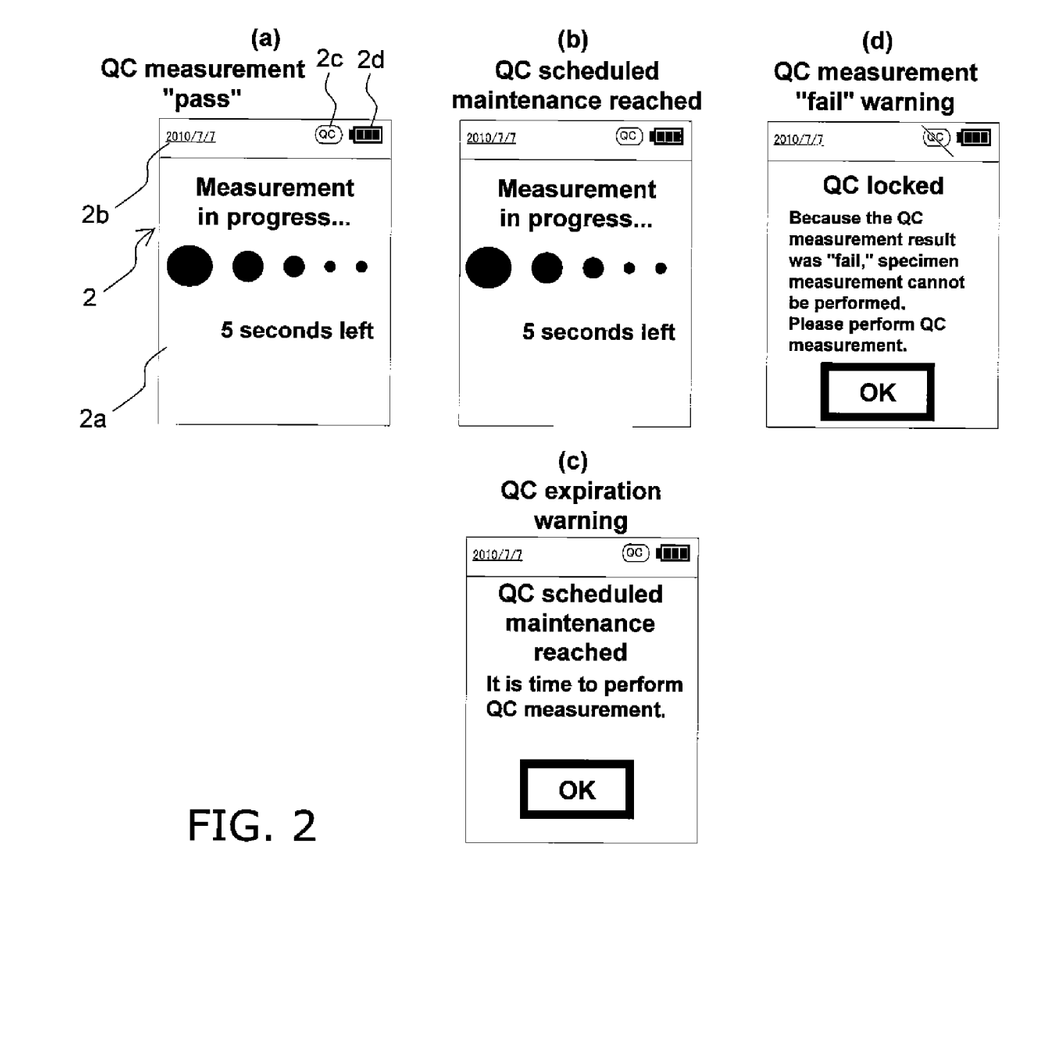
FIGS. 2a to 2d are diagrams of what is displayed on the display section of the biological sample measuring device in FIG. 1.

FIG. 2a shows what is displayed on the display section 2 when the measurement of blood glucose is performed within the quality control effective period of the biological sample measuring device being used.

As shown in FIG. 2a, with the biological sample measuring device in this embodiment, the display screen of the display section 2 is divided into a first display area 2a for displaying measurement values such as blood glucose level, and a second display area 2b for displaying symbols indicating the current date and time, the operating status, and so forth.

The first display area 2a is the main display area for displaying measurement results for blood glucose level and so on, and is larger in surface area than the second display area 2b.

In FIG. 2a, it is displayed in the first display area 2a that blood glucose level is being measured, and that this measurement will take 5 more seconds.

Meanwhile, the current date and time, a quality control scheduled maintenance valid mark 2c, and a remaining battery charge display 2d for the battery 13 are displayed in the second display area 2b.

In FIG. 2a, the scheduled maintenance valid mark 2c is displayed in black letters, for example. This means that the biological sample measuring device being used is still within its quality control scheduled maintenance.

FIG. 2b shows what is displayed on the display section 2 when a blood glucose level is measured on the quality control scheduled maintenance of the biological sample measuring device being used.

Specifically, in this embodiment, when the quality control scheduled maintenance is reached for the biological sample measuring device, as shown in FIG. 2b, the display color of the scheduled maintenance valid mark 2c changes from black to read in the second display area 2b. This tells the user that the biological sample measuring device being used has reached its quality control scheduled maintenance.

Also, in the management of the quality control scheduled maintenance of a biological sample measuring device, whether or not a specific length of time has elapsed since the previous quality control measurement is determined on the basis of the current date and time acquired by the time acquisition section 15, and the date of the previous quality control measurement recorded to the recorder 16.

A warning display for quality control expiration may be given after the quality control scheduled maintenance has passed, or it may be set to be given one to three days before the scheduled maintenance.

FIG. 2c shows what is displayed on the display section 2 when an attempt is made to measure a blood glucose level on the quality control scheduled maintenance for the biological sample measuring device being used.

Here, just as in FIG. 2b, the letting of the scheduled maintenance valid mark 2c is displayed in red rather than black in the second display area 2b of the display screen of the display section 2, and in the first display area 2a a warning display is given indicating that the quality control scheduled maintenance has been reached.

Specifically, in this embodiment, when the quality control scheduled maintenance of the biological sample measuring device has been reached, as shown in FIG. 2c, a warning display about reaching the scheduled maintenance is given in the first display area 2a, with background color changed from the normal display color used before the quality control scheduled maintenance to red. This reliably tells the user that the biological sample measuring device being used as reached its quality control scheduled maintenance.

In this embodiment, the warning display in the first and second display areas 2a and 2b is controlled so that it is only given the first time the device is turned on that day. That is, with the biological sample measuring device in this embodiment, when the quality control scheduled maintenance is reached, the display shown in FIG. 2c is shown only the first time the biological sample measuring device is turned on that day, and the display shown in FIG. 2b is shown the second and subsequent times it is turned on that day, on the basis of the date and time information acquired by the time acquisition section 15.

Consequently, even when a nurse or other such user measures the blood glucose level of patients repeatedly in a specific time slot at a hospital or other such medical institution, since a warning display is shown in the first display area 2a only the first time the device is turned on that day, the warning display in the first display area 2a only has to be deleted the first time the device is used for measurement. As a result, there will be no warning display in the first display area 2a the second and subsequent times the device is turned on that day, so the user does not need to delete the warning display every time the device is turned on. Thus, the device is more convenient for the user to use when it is repeatedly used in a specific time slot at a hospital or other such medical institution (that is, when the usage frequency is higher during a specific time slot).

Also, the second and subsequent times the device is turned on that day, the scheduled maintenance valid mark 2c will always be displayed in red letters in the second display area 2b unless measurement is performed for operational confirmation. Consequently, even though measurement for operational confirmation is not performed as soon as the warning display appears, the user will not forget about the warning display and fail to check on the operation for an extended period.

The flow of display control related to the warning display in the first and second display areas 2a and 2b will be discussed in detail at a later point.

FIG. 2d shows what is displayed on the display section 2 when an attempt is made to measure a blood glucose level when the biological sample measuring device being used has reached its quality control scheduled maintenance, or when a specific length of time has passed since the scheduled maintenance.

Here, the first display area 2a of the display screen of the display section 2 shows a locked state due to the fact that the quality control scheduled maintenance has been exceeded while the background color has been changed to red, or the quality control measurement (QC measurement) has failed, and the second display area 2b shows that no further measurement of blood glucose level is possible by displaying a red diagonal line over the scheduled maintenance valid mark 2c displayed in red.

Specifically, in this embodiment, if the quality control scheduled maintenance of the biological sample measuring device has been reached, or if a specific length of time has elapsed since this scheduled maintenance, or if the quality control measurement itself has failed, a locked state is displayed so that no further measurement can be performed, in order to prevent repeated measurement from being performed in a state of diminished measurement accuracy. This urges the user to release the locked state and perform measurement for operational confirmation in order to continue further sample measurements.

This locked state can be released once quality control measurement is performed again and the quality control measurement passes.

Figure 4:
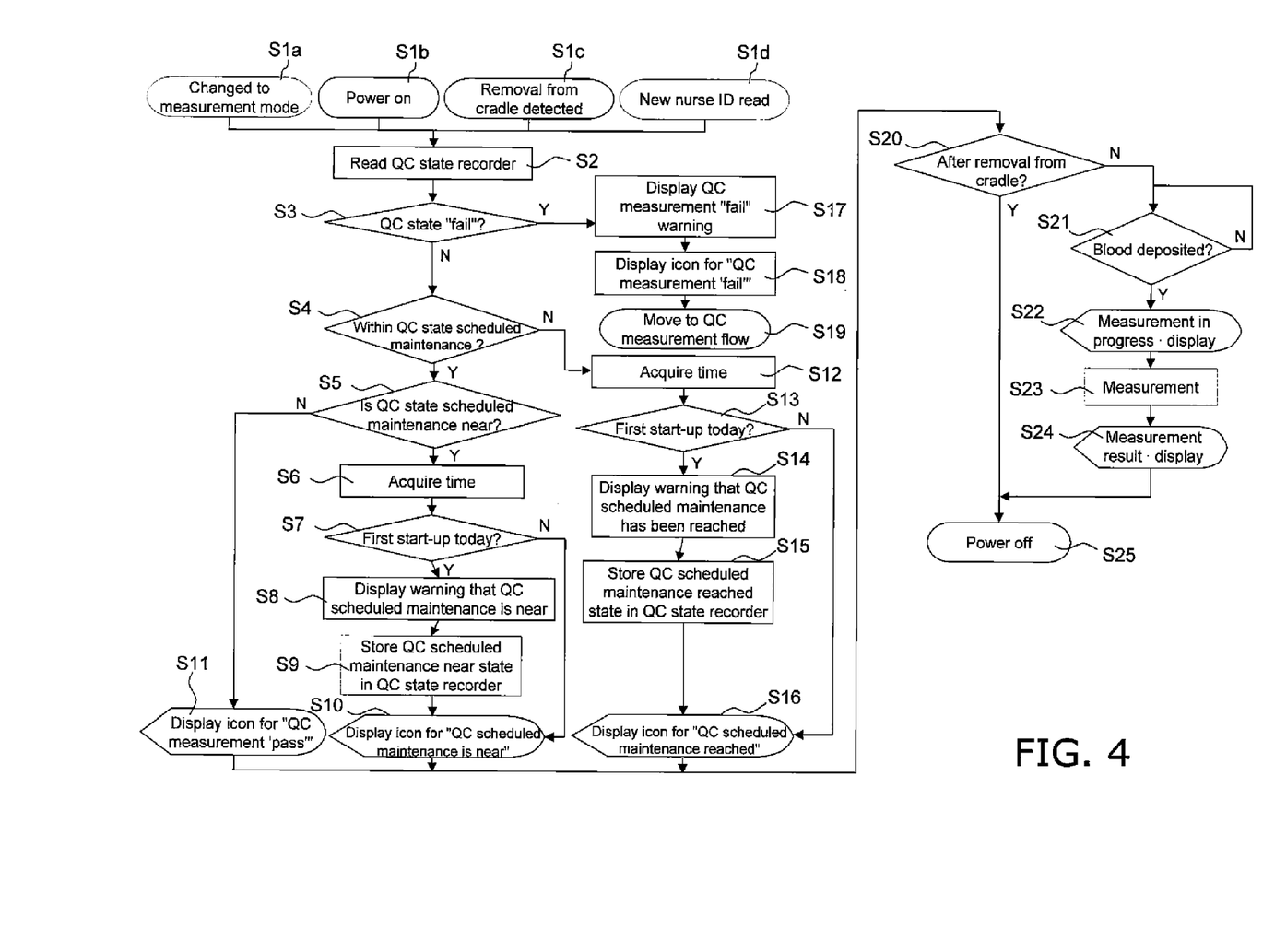
FIG. 4 is an operation flowchart of the biological sample measuring device in FIG. 1.

Display Control Related to Quality Control Scheduled Maintenance with this Biological Sample Measuring Device FIG. 4 is a flowchart of display control related to a quality control scheduled maintenance with the biological sample measuring device in this embodiment.

As shown in FIG. 4, the controller 9 acquires quality control scheduled maintenance information from the recorder 16 (step 2) when, for example, the biological sample measuring device has been changed to measurement mode (step 1a), when the power button 3 has been switched on (step 1b), when it is detected that the main body case 1 has been removed from its cradle (not shown) (step 1c), or when the nurse ID of the person conducting the measurement has been newly read (step 1d).

In step 1c, whether or not the main body case 1 is in its cradle is determined from the conduction state to the charging terminal 14.

Then, in step 3, the controller 9 acquires information related to the most recent quality control state (QC state) from the recorder 16, and determines whether or not a warning display is necessary to the effect that the scheduled maintenance is approaching, or has already arrived, or a specific length of time has elapsed since the scheduled maintenance.

In step 3, the flow proceeds to step 4 if it is determined that the QC state is not "failed." On the other hand, the flow proceeds to step 17 if it is determined that the QC state is "failed."

If the QC state here is "failed," that refers to the above-mentioned locked state.

Then, in step 5, if the device has not yet reached its scheduled maintenance, the controller 9 determines whether or not the scheduled maintenance is near.

If the scheduled maintenance is determined to be near, the flow proceeds to step 6. On the other hand, if the scheduled maintenance is determined not to be near, the flow proceeds to step 11.

Then, in step 6, the controller 9 acquires time information from the time acquisition section 15.

Then, in step 7, the controller 9 determines whether or not the current start-up is the first one that day on the basis of the time information acquired in step 6.

Here, if it is determined that this is the first start-up, the flow proceeds to step 8. On the other hand, if it is determined that this is not the first start-up, the flow proceeds to step 10.

Then, in step 8, the controller 9 displays on the display section 2 a warning to the effect that the quality control scheduled maintenance is near.

Figure 7:
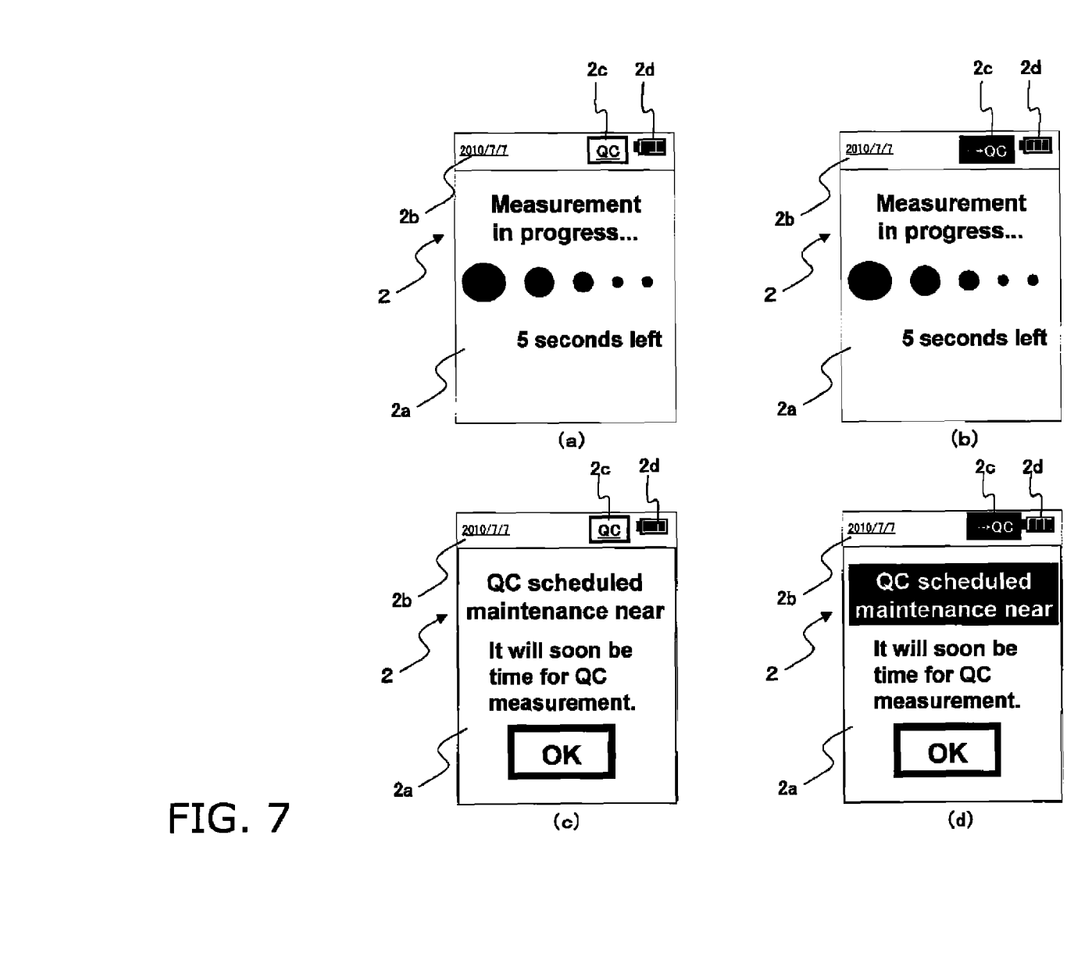
FIGS. 7a to 7d are diagrams of what is displayed on the display section of the biological sample measuring device pertaining to yet another embodiment of the present invention.

As shown in FIG. 7c, the warning display indicating that the scheduled maintenance is near may be a display of "quality control scheduled maintenance is near," "it is nearly time for QC measurement," or the like in the first display area 2a.

Then, in step 9, the controller 9 records the quality control expiration state to the recorder 16.

Then, in step 10, the controller 9 displays in the second display area 2b of the display section 2 an icon indicating that the quality control scheduled maintenance is near.

As shown in FIG. 7a, display control indicating that the quality control scheduled maintenance is near may be accomplished by a display in which the letters of the scheduled maintenance valid mark 2c are enclosed in a box, or the display color is yellow or orange, etc.

Then, in step 11, the controller 9 displays the scheduled maintenance valid mark 2c in black in the second display area 2b as shown in FIG. 2a.

Then, in step 20, it is determined whether or not the current state is one in which the main body case 1 has been removed from its cradle.

If it is determined that it has been removed from its cradle, it is assumed that the user does not intend to measure a blood glucose level at that point, and the power is turned off in step 25.

On the other hand, if that is not the case, such as if it is determined in step 1 that the power button 3 has been switched on, then it is determined that the user intends to measure a blood glucose level, etc., and the flow moves to step 21.

That is, in step 21, it is determined whether or not a patient's blood has been deposited on the blood deposition section of the sensor in a state in which the sensor has been inserted into the sensor insertion opening 7. If blood has been deposited, in step 22 the controller 9 displays on the display section 2 a display to the effect that measurement is in progress.

Then, in step 23, measurement of blood glucose level is performed by the measurement section 10.

Then, in step 24, this measurement result is displayed in the first display area 2a of the display section 2, and in step 25 the power to the biological sample measuring device is turned off.

In the above-mentioned step 4, it is determined whether or not the current time (date and time) acquired from the time acquisition section 15 is before the quality control scheduled maintenance.

Therefore, if the current time (date and time) indicates that the quality control scheduled maintenance has been reached, the controller 9 again acquires the current time from the time acquisition section 15 in step 12.

In step 13, it is determined whether or not the re-acquired time (date and time) is the first start-up that day.

If it is determined here that this is the first start-up of the day, in step 14 a warning display is given in the first display area 2a indicating that quality control scheduled maintenance is near, as shown in FIG. 2c. On the other hand, if it is determined to be the second or subsequent start-up that day, step 14 and step 15 are skipped, and the flow moves to step 16.

Then, in step 15 the controller 9 records the quality control expired state to the recorder 16.

Then, in step 16, the controller 9 changes the display color of the scheduled maintenance valid mark 2c in the second display area 2b from black to red, and gives a warning display indicating that the quality control scheduled maintenance has been reached, as shown in FIG. 2b.

Specifically, with the biological sample measuring device in this embodiment, if the quality control scheduled maintenance has been reached or is near, a warning display to the effect that the scheduled maintenance has been reached or is near is given in the first and second display areas 2a and 2b the first time the device is turned on that day, in order to urge the user to perform measurement for operational confirmation. The second and subsequent times the device is turned on that day, the scheduled maintenance valid mark 2c is displayed in red, etc., only in the second display area 2b. That is, the second and subsequent times the device is turned on that day, no warning display is given in the first display area 2a, and a screen that allows measurement is displayed right away.

Also, since a warning display is given in the first display area 2a (which displays measurement values) only at the first start-up of the day, the user doesn't have to bother with canceling this warning display every time. Consequently, a biological sample measuring device is provided that is convenient to use even when blood glucose level or the like is measured repeatedly in a specific time slot in a hospital or other such medical institution.

Furthermore, when the scheduled maintenance has been reached or is near, even though the warning display disappears from the first display area 2a the second and subsequent times the device is turned on that day, the warning display is always displayed in the second display area 2b. This prevents the user from forgetting about the warning display that was shown in the first display area 2a at the first start-up, which would result in the biological sample measuring device becoming unusable after the quality control scheduled maintenance was exceeded.

In the above-mentioned step 3, if it is determined that the QC measurement was "failed" (failed QC state), in which the biological sample measuring device has already reached its quality control scheduled maintenance or a specific length of time has elapsed since the scheduled maintenance, the controller 9 displays that the scheduled maintenance has been reached in the first display area 2a in step 17, as shown in FIG. 2d.

At this point, the background of the first display area 2a is changed to a different color (such as pink or another color that gives the impression of warning), which improves visibility and evokes caution.

Next, in step 18 the controller 9 displays a red diagonal line over the scheduled maintenance valid mark 2c in the second display area 2b, and moves to a locked state in which any further measurement of blood glucose level is prohibited.

Therefore, the user has to perform a reference sample measurement for operational confirmation in step 19 in order to use the biological sample measuring device again.

Figure 5:
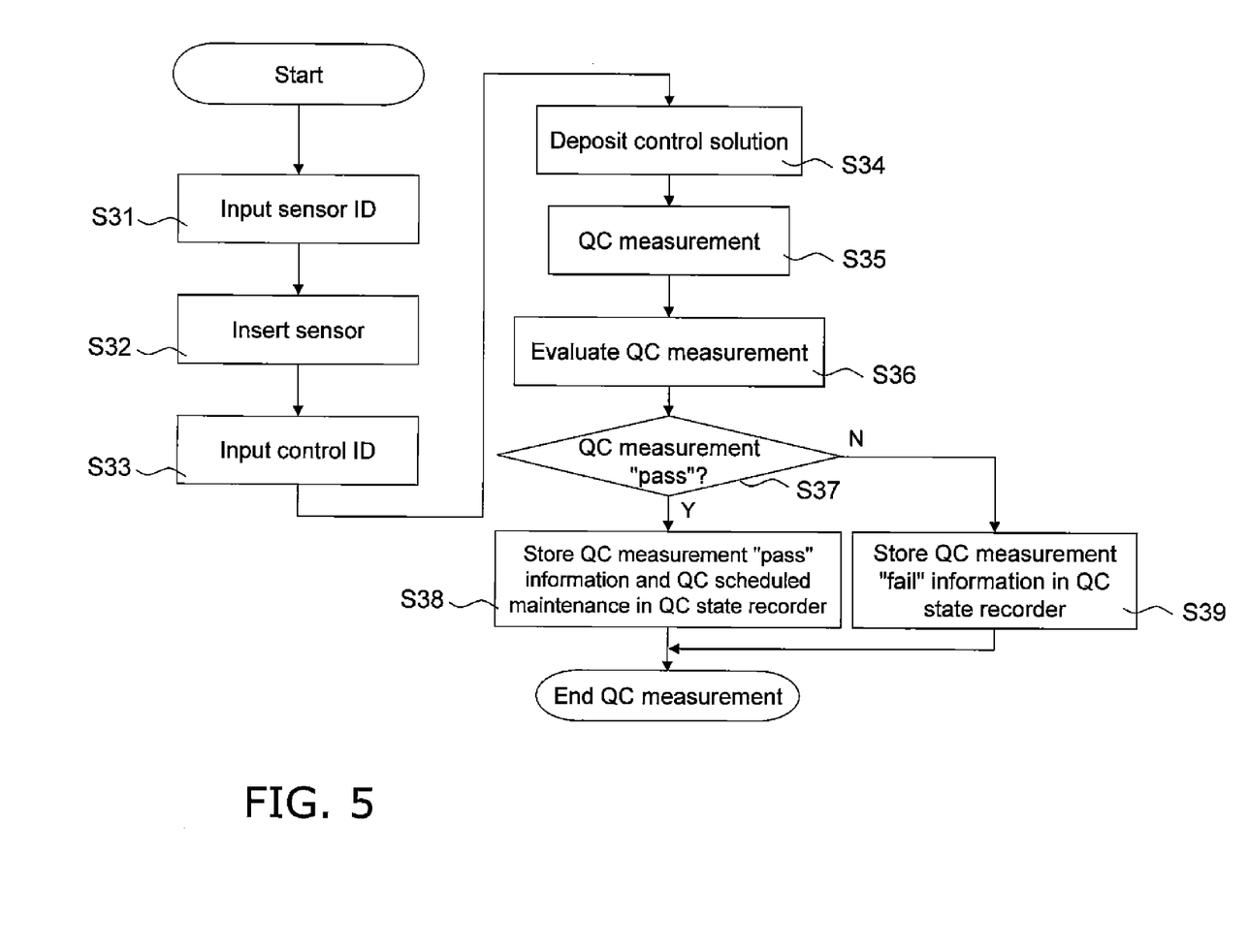
FIG. 5 is an operation flowchart of the biological sample measuring device in FIG. 1.

FIG. 5 is a flowchart of this reference sample (control solution) measurement (QC measurement) for operational confirmation.

Specifically, as shown in FIG. 5, when this reference sample measurement mode is commenced, in step 31 a sensor ID provided to a sensor bottle is inputted by the barcode reader 11.

After this, in step 32, the sensor is taken out of the sensor bottle and inserted into the sensor insertion opening 7.

Then, in step 33, the reference sample ID provided to the container or package of the reference sample (control solution) deposited on the blood deposition section of the sensor is inputted by the barcode reader 11.

Consequently, the type of control solution (high, middle, or low) can be determined Then, when the reference sample is deposited on the blood deposition section in step 34, measurement is performed by the measurement section 10 in step 35.

In step 36 the controller 9 determines whether or not this measurement result is the proper value.

Here, if it is determined that the measurement result is the proper value, in step 37 the QC measurement is determined to be "pass," and in step 38 the quality control scheduled maintenance for one month later is recorded to the recorder 6.

Meanwhile, if it is determined in step 37 that the measurement result is not the proper value, in step 39 QC measurement "fail" information indicating that the result is outside the quality control limit is recorded to the recorder 16, and this biological sample measuring device is rendered unusable (locked).

This ends the reference sample measurement mode for quality control.

Other Embodiments

An embodiment of the present invention was described above, but the present invention is not limited to or by the above embodiment, and various modifications are possible without departing from the gist of the invention.

(A)

In the above embodiment, an example was given in which a warning display of the quality control scheduled maintenance was shown in both the first and second display areas 2a and 2b only the first time the device was turned on that day, and the warning display was shown only in the second display area 2b (a sub-display area) the second and subsequent times the device was turned on that day. However, the present invention is not limited to this.

The condition for showing the warning display in both the first and second display areas 2a and 2b is not limited to being the first start-up of the day, and instead, for example, the warning display may be shown in both of the above areas the first time the device is turned on after the biological sample measuring device is placed in its cradle for charging.

Consequently, when another user uses the biological sample measuring device to perform measurement after the device has been charged in its cradle, the warning display is shown in the above two areas, allowing a new user to be reliably advised that the scheduled maintenance has been reached or is near.

Also, the nurse or the like who is the user in a hospital or other such medical institution has a unique ID, and measurement is performed after this ID is read by the barcode reader 11 or the like when the biological sample measuring device is to be used. Therefore, new users also need to be advised that the biological sample measuring device has reached its quality control scheduled maintenance, so the warning display may be shown in both of the above areas when the device is turned on for the first time after a new ID is read (after the user changes).

(B)

In the above embodiment, for the way to change the display method of the scheduled maintenance valid mark 2c in the second display area 2b, an example was given in which the color of the letters was changed from black to red on or near the quality control scheduled maintenance, but the present invention is not limited to this.

For example, the way to change the display method of the scheduled maintenance valid mark 2c in the second display area 2b may be to change the letters from black to some other color, rather than changing them from black to red.

(C)

In the above embodiment, for the way to change the display method of the scheduled maintenance valid mark 2c in the second display area 2b, an example was given in which the color of the color of the letters was changed from black to red on or near the quality control scheduled maintenance, but the present invention is not limited to this.

Figure 6:
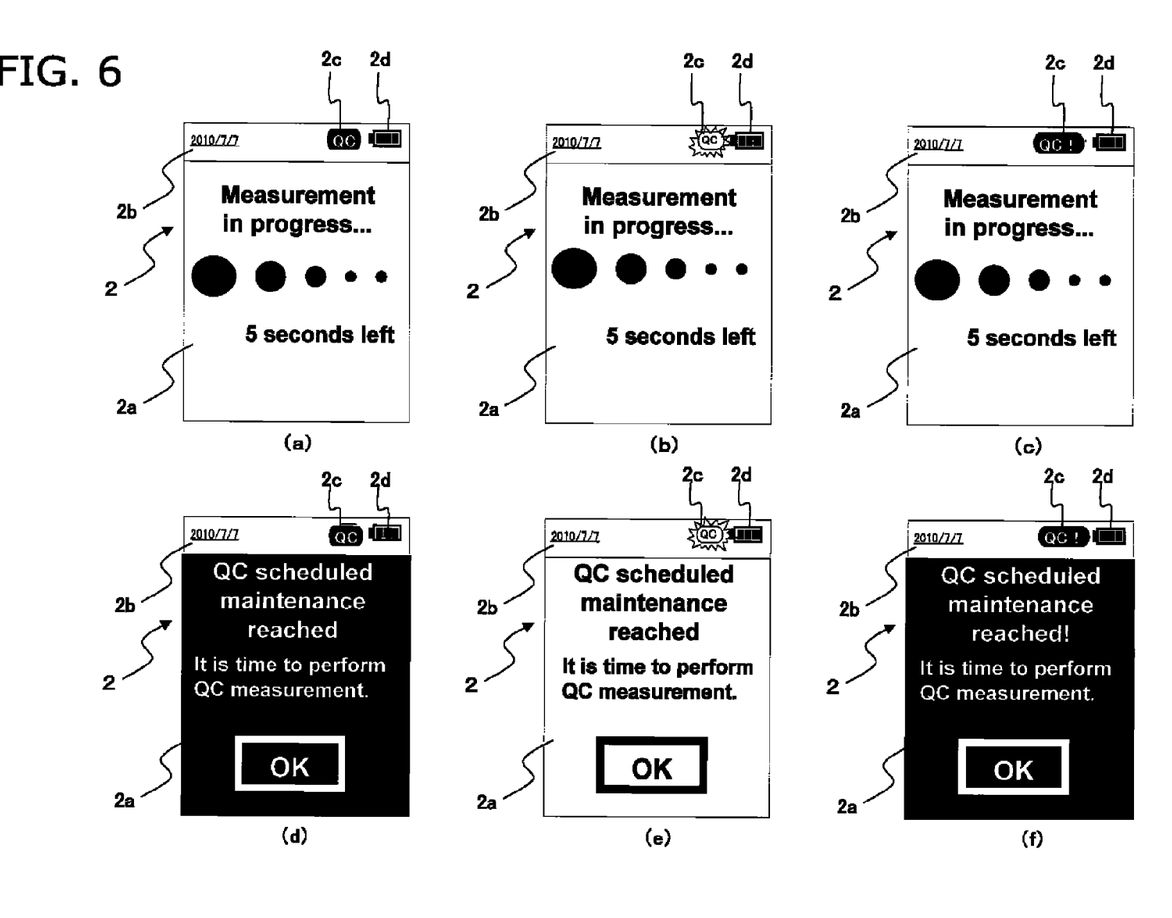
FIGS. 6a to 6f are diagrams of what is displayed on the display section of the biological sample measuring device pertaining to another embodiment of the present invention.

For example, as shown in FIG. 6a, rather than changing the color of the letters, the scheduled maintenance valid mark 2c may be displayed in knock-out print on or near the quality control scheduled maintenance.

Also, as shown in FIG. 6b, on or near the quality control scheduled maintenance, the letters may be displayed flashing in addition to changing their color to red.

Furthermore, as shown in FIG. 6c, on or near the quality control scheduled maintenance, an exclamation mark or other such mark that stands out may be added to the display next to the scheduled maintenance valid mark 2c displayed in the second display area 2b.

It is best if the color of the warning display is some color other than that used in the normal display.

(D)

In the above embodiment, an example was given in which a warning display was given when the quality control scheduled maintenance was reached, for the way to change the display method in the first display area 2a at the point when the device is first turned on that day, or when the ID of a new nurse is read, or when the mode is returned to measurement mode, or when the device is removed from its cradle. However, the present invention is not limited to this.

For example, as shown in FIG. 6d, the first display area 2a (main display area) may also be displayed in knock-out print.

Also, as shown in FIG. 6e, the first display area 2a may also be displayed flashing.

Furthermore, as shown in FIG. 6f, an exclamation mark or other such mark that stands out may be added to the display of "expired" in the first display area 2a.

It is best if the color of the warning display is some color other than that used in the normal display.

The display in the first display area 2a may be a combination of what is shown in FIGS. 6d and 6f, such as a knock-out display that is flashing.

(E)

In the above embodiment, for the way to change the display method of the scheduled maintenance valid mark 2c in the second display area 2b, an example was given in which the letters of the scheduled maintenance valid mark 2c are enclosed in a box as shown in FIG. 7a when the quality control scheduled maintenance is near. However, the present invention is not limited to this.

For example, as shown in FIG. 7b, an arrow may be added next to the scheduled maintenance valid mark 2c displayed in the second display area 2b.

Here again, the user can easily recognize that the quality control scheduled maintenance of the biological sample measuring device is approaching.

(F)

In the above embodiment, an example was given in which a warning display to the effect that "quality control scheduled maintenance is near" was given as shown in FIG. 7c, for the way to change the display method in the first display area 2a at the point when the device is first turned on that day, or when the ID of a new nurse is read, or when the mode is returned to measurement mode, or when the device is removed from its cradle. However, the present invention is not limited to this.

For example, as shown in FIG. 7d, text reading "quality control scheduled maintenance is near" may be displayed inverted as knock-out print.

Alternatively, display control in which text reading "quality control scheduled maintenance is near" may be displayed flashing, or is changed to a color that stands out, or the like, may be combined.

This allows user to easily recognize that the quality control scheduled maintenance of the biological sample measuring device is approaching.

(G)

In the above embodiment, an example was given in which a biological sample measuring device was used to measure a blood glucose level using a patient's blood deposited on a sensor, but the present invention is not limited to this.

For example, the biological sample measuring device of the present invention need not be a blood glucose meter for measuring only blood glucose levels, and may instead be a device that measures other biological samples, such as a lactic acid meter that measures lactic acid.

With the biological sample measuring device for medical institutions of the present invention, since a warning display is shown in a first display area for displaying measurement values only the first time the device is turned on that day, the user does not have to bother with canceling this warning display every time the device is used, which makes it more convenient. Also, on or near the quality control scheduled maintenance, unless measurement for operational confirmation is performed, the warning display is always displayed in a second display area, which prevents the quality control scheduled maintenance from being exceeded. Thus, because the above effect is obtained, the present invention can be widely applied to various kinds of measurement device used repeatedly at a specific time slot in hospitals or other such medical institutions.

REFERENCE SIGNS LIST 1 main body case
2 display section
2a first display area
2b second display area
2c scheduled maintenance valid mark
2d remaining battery charge display
3 power button
4 menu button
5 cross key
6 enter button
7 sensor insertion opening
8 sensor eject lever
9 controller
10 measurement section
11 barcode reader (ID acquisition section)
12 input section
13 battery
14 charging terminal
15 time acquisition section
16 recorder
17 sensor mounting portion

The invention claimed is:

1. A biological sample measuring device for medical institutions, comprising:
    a main body case having a display;
    a sensor mounting portion that is provided to a first end of the main body case and to which is mounted a sensor for measuring biological samples;
    a measurement section that is connected to the sensor mounting portion and is used to measure biological samples;
    a non-transitory memory device storing a program; and
    a controller that executes the program that causes a display section to display scheduled maintenance warnings regarding scheduled maintenance for the biological measuring device in a first display area and a second display area at initial start-up that satifies a specific condition on the scheduled maintenance or shortly before, and display a biological sample measurement value in the first display area and a scheduled maintenance warning regarding scheduled maintenance for the biological sample measuring device only in the second display area at the second and subsequent start-ups on the same day,
    wherein the scheduled maintenance warnings displayed in the first display area are operable to cancel the scheduled maintenance warnings displayed by a user.

2. The biological sample measuring device for medical institutions according to claim 1,
    wherein the specific condition includes a case in which the date has changed.

3. The biological sample measuring device for medical institutions according to claim 1,
    wherein the specific condition includes a case in which the main body case has been placed in a holder.

4. The biological sample measuring device for medical institutions according to claim 1,
    further comprising an ID acquisition section that reads the ID of a measurement technician,
    wherein the specific condition includes a case in which the ID of the measurement technician has changed.

5. The biological sample measuring device for medical institutions according to claim 1,
    wherein the controller displays a scheduled maintenance valid mark in the second display area, and changes the display color of the scheduled maintenance valid mark on the scheduled maintenance or shortly before.

6. The biological sample measuring device for medical institutions according to claim 5,
    wherein the controller displays in the first display area a scheduled maintenance warning of the same or similar color as the display color of the scheduled maintenance valid mark displayed in the second display area on the scheduled maintenance or shortly before.

7. The biological sample measuring device for medical institutions according to claim 1,
    wherein the controller displays a scheduled maintenance valid mark in the second display area, and flashes the scheduled maintenance valid mark on the scheduled maintenance or shortly before.

8. The biological sample measuring device for medical institutions according to claim 1,
    wherein the first display area is larger than the second display area.

9. The biological sample measuring device for medical institutions according to claim 8,
    wherein the second display area is disposed along the upper edge of the display screen of the display section.

10. The biological sample measuring device for medical institutions according to Claim 1,
    wherein the controller displays only in the second display area when the quality control measurement is "pass.".

* * * * *